United States Patent
Morgan et al.

(10) Patent No.: US 9,671,379 B2
(45) Date of Patent: Jun. 6, 2017

(54) SYSTEMS AND METHODS FOR ANALYZING CONTAMINANTS IN FLOWING ATMOSPHERIC AIR

(71) Applicant: Halliburton Energy Services, Inc., Houston, TX (US)

(72) Inventors: Rickey Lynn Morgan, Duncan, OK (US); Danny Keith Mints, Duncan, OK (US); Paul Lewis Mendenall, Duncan, OK (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 5 days.

(21) Appl. No.: 14/536,895

(22) Filed: Nov. 10, 2014

(65) Prior Publication Data
US 2016/0131623 A1     May 12, 2016

(51) Int. Cl.
*G01N 21/53*     (2006.01)
*G01N 33/00*     (2006.01)
*G01N 21/85*     (2006.01)

(52) U.S. Cl.
CPC ......... *G01N 33/0004* (2013.01); *G01N 21/53* (2013.01); *G01N 21/534* (2013.01); *G01N 21/85* (2013.01)

(58) Field of Classification Search
CPC .... G01N 21/01; G01N 33/0004; G01N 21/53; G01N 21/534; G01N 21/85; G01N 21/51
See application file for complete search history.

(56) References Cited

U.S. PATENT DOCUMENTS

| | | | |
|---|---|---|---|
| 6,176,323 B1 * | 1/2001 | Weirich | E21B 21/08 175/40 |
| 6,198,531 B1 | 3/2001 | Myrick et al. | |
| 6,529,276 B1 | 3/2003 | Myrick | |
| 7,123,844 B2 | 10/2006 | Myrick | |
| 7,834,999 B2 | 11/2010 | Myrick et al. | |
| 7,911,605 B2 | 3/2011 | Myrick et al. | |

(Continued)

FOREIGN PATENT DOCUMENTS

| | | |
|---|---|---|
| WO | 2013022535 A2 | 2/2013 |
| WO | 2013022549 A1 | 2/2013 |

(Continued)

OTHER PUBLICATIONS

Siegel et al., "Common Organic Contaminants in Cement and Bentonite Used for Water and Monitoring Well Construction," Chesapeake Energy, Jul. 10, 2013.

(Continued)

*Primary Examiner* — David Porta
*Assistant Examiner* — Faye Boosalis
(74) *Attorney, Agent, or Firm* — McDermott Will & Emery LLP

(57) ABSTRACT

Optically interacting electromagnetic radiation with a flowing atmospheric air composition and optically interacting the electromagnetic radiation with an integrated computational element ("ICE"), the ICE being configured to analyze for a contaminant in the flowing atmospheric air. A detector receives the electromagnetic radiation that has optically interacted with the flowing atmospheric air and the ICE and generates an output signal corresponding to a characteristic of the contaminant in the flowing atmospheric air.

17 Claims, 5 Drawing Sheets

(56) References Cited

U.S. PATENT DOCUMENTS

| | | |
|---|---|---|
| 7,920,258 B2 | 4/2011 | Myrick et al. |
| 8,049,881 B2 | 11/2011 | Myrick et al. |
| 8,575,541 B1 | 11/2013 | Jamison et al. |
| 8,619,256 B1 | 12/2013 | Pelletier et al. |
| 8,760,644 B2 | 6/2014 | Seckar |
| 8,765,061 B2 | 7/2014 | Tunheim et al. |
| 8,780,352 B2 | 7/2014 | Freese et al. |
| 8,812,238 B2 | 8/2014 | Ljungdahl et al. |
| 8,823,939 B2 | 9/2014 | Freese et al. |
| 2009/0073433 A1 | 3/2009 | Myrick et al. |
| 2009/0182693 A1 | 7/2009 | Fulton et al. |
| 2009/0219538 A1 | 9/2009 | Myrick et al. |
| 2009/0219539 A1 | 9/2009 | Myrick et al. |
| 2013/0031964 A1 | 2/2013 | Tunheim et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032334 A1 | 2/2013 | Freese et al. |
| 2013/0032338 A1 | 2/2013 | Kalia et al. |
| 2013/0032339 A1 | 2/2013 | Kalia et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0032545 A1 | 2/2013 | Freese et al. |
| 2013/0032736 A1 | 2/2013 | Tunheim et al. |
| 2013/0033701 A1 | 2/2013 | Tunheim et al. |
| 2013/0033702 A1 | 2/2013 | Tunheim et al. |
| 2013/0034842 A1 | 2/2013 | Tunheim et al. |
| 2013/0035262 A1 | 2/2013 | Freese et al. |
| 2013/0284894 A1 | 10/2013 | Freese et al. |
| 2013/0284895 A1 | 10/2013 | Freese et al. |
| 2013/0284896 A1 | 10/2013 | Freese et al. |
| 2013/0284897 A1 | 10/2013 | Freese et al. |
| 2013/0284898 A1 | 10/2013 | Freese et al. |
| 2013/0284899 A1 | 10/2013 | Freese et al. |
| 2013/0284904 A1 | 10/2013 | Freese et al. |
| 2013/0286398 A1 | 10/2013 | Freese et al. |
| 2013/0286399 A1 | 10/2013 | Freese et al. |
| 2014/0061449 A1 | 3/2014 | Tunheim et al. |
| 2014/0061513 A1 | 3/2014 | Tunheim et al. |
| 2014/0067268 A1 | 3/2014 | Tunheim et al. |
| 2014/0076549 A1 | 3/2014 | Pelletier et al. |
| 2014/0076550 A1 | 3/2014 | Pelletier et al. |
| 2014/0076551 A1 | 3/2014 | Pelletier et al. |
| 2014/0078499 A1 | 3/2014 | Tunheim et al. |
| 2014/0080172 A1 | 3/2014 | Tunheim et al. |
| 2014/0080223 A1 | 3/2014 | Tunheim et al. |
| 2014/0081594 A1 | 3/2014 | Tunheim et al. |
| 2014/0110105 A1 | 4/2014 | Jones et al. |
| 2014/0166361 A1 | 6/2014 | Jamison et al. |
| 2014/0166871 A1 | 6/2014 | Jamison et al. |
| 2014/0172177 A1 | 6/2014 | Jamison et al. |
| 2014/0202689 A1 | 7/2014 | Walton et al. |
| 2014/0231071 A1 | 8/2014 | Walton et al. |

FOREIGN PATENT DOCUMENTS

| | | |
|---|---|---|
| WO | 2013022556 A2 | 2/2013 |
| WO | 2013022558 A2 | 2/2013 |
| WO | 2013022568 A2 | 2/2013 |
| WO | 2013022569 A1 | 2/2013 |
| WO | 2013022570 A2 | 2/2013 |
| WO | 2013022574 A2 | 2/2013 |
| WO | 2013022588 A2 | 2/2013 |
| WO | 2014093629 A1 | 6/2014 |

OTHER PUBLICATIONS

B. T. Sullivan and J. A. Dobrowolski, "Implementation of a numerical needle method for thin-film design," Appl. Opt. 35, 5484-5492 (1996).

J. A. Dobrowolski and R. A. Kemp, "Refinement of optical multilayer systems with different optimization procedures," Appl. Opt. 29, 2876-2893 (1990).

* cited by examiner

SYSTEMS AND METHODS FOR ANALYZING CONTAMINANTS IN FLOWING ATMOSPHERIC AIR

BACKGROUND

The exemplary embodiments described herein relate to optical analysis systems and methods for flowing atmospheric air and, in particular, to systems and methods for analyzing contaminants present in flowing atmospheric air using an integrated computational element.

Flowing atmospheric air (also referred to herein simply as "flowing air"), such as that produced by an air compressor, is used in various aspects of an oil and gas application including, for example, drying powder compositions (e.g., cements, weighting agents, proppant, and the like) to an appropriate moisture content, supplying air to a clean room environment for oil and gas testing operations, supplying air to a treatment fluid for use in drilling, stimulation, and/or other subterranean formation operations, and the like.

The presence of contaminants (e.g., liquid, gaseous, biological, and/or dry contaminants) in flowing air may adversely affect the ability of the flowing air to perform its function (e.g., to remove moisture, to keep areas free of impurities, and the like) or may adversely affect the ability of another composition (e.g., powder composition, treatment fluid, and the like) to perform its function. In such instances, the presence of the contaminants may result in significant delay and or expense in the form of operator time and/or remedial measures of a subterranean formation operation or related oil and gas operation, whether in the field or laboratory, for example, to remove the contaminant(s).

As an example, flowing atmospheric air may be used to dry a cement composition used to form a cement column in a wellbore in a subterranean formation. The presence of contaminants introduced into the cement composition from the flowing air may result in a loss of structural integrity to the later set cement, such as by preventing complete cement hydration, permitting other fluids (e.g., formation fluids, for example) to permeate into the sealing or set cement, and the like. In such instances, the set cement may be incapable of providing zonal isolation, preventing casing collapse and/or stuck pipe, plugging a wellbore, and/or other functionalities the set cement is intended to perform. Accordingly, the presence of such contaminants may be particularly detrimental to a particular operation if a cement composition includes one or more contaminants in an unacceptable amount, and the resultant set cement may require costly, time-consuming remedial measures.

BRIEF DESCRIPTION OF THE DRAWINGS

The following figures are included to illustrate certain aspects of the exemplary embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
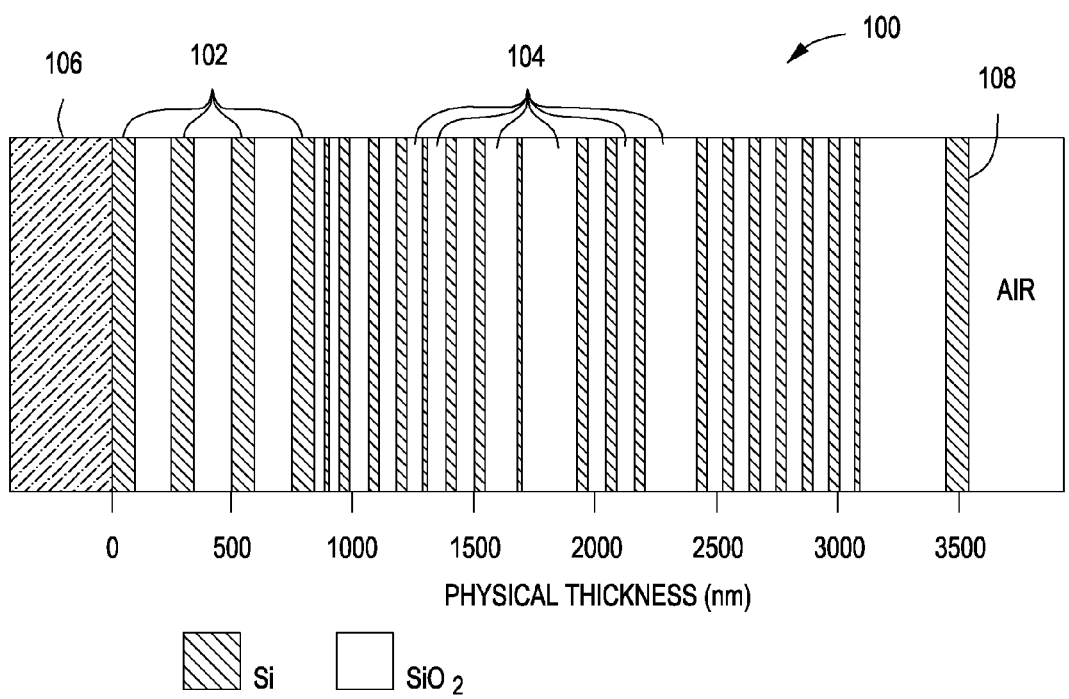
FIG. 1 illustrates an exemplary integrated computation element, according to one or more embodiments described herein.

The exemplary embodiments described herein relate to optical analysis systems and methods for flowing atmospheric air and, in particular, to systems and methods for analyzing contaminants present in flowing atmospheric air using an integrated computational element.

The exemplary systems and methods described herein employ various configurations of optical computing devices, also commonly referred to as "opticoanalytical devices," for the rapid analysis of contaminants in flowing atmospheric air. The disclosed systems and methods may be suitable for use in the oil and gas industry since the described optical computing devices provide a cost-effective, rugged, and accurate means for identifying one or more contaminants in flowing air in order to facilitate oil and gas production and/or safety of oil and gas wells. It will be appreciated, however, that the various disclosed systems and methods are equally applicable to other technology fields including, but not limited to, the food and drug industry, industrial applications, mining industries, or any field where it may be advantageous to determine in real-time or near real-time a characteristic of a contaminant in flowing atmospheric air. As used herein, the term "flowing" refers to circulation or movement of air with reference to the optical computing devices disclosed herein. That is, the flowing air itself may be moving. As used herein, the term "atmospheric," used interchangeably with "air," refers to atmospheric gases surrounding Earth, typically composed primary of nitrogen, oxygen, argon, and carbon dioxide, among other gases and liquid components (e.g., water vapor).

One or more illustrative embodiments incorporating the disclosure herein are presented below. Not all features of an actual implementation are described or shown in this application for the sake of clarity. It is to be understood that in the development of an actual embodiment incorporating the present disclosure, numerous implementation-specific decisions must be made to achieve the developer's goals, such as compliance with system-related, business-related, government-related and other constraints, which may vary by implementation and from time to time. While a developer's efforts might be complex and time-consuming, such efforts would be, nevertheless, a routine undertaking for one having ordinary skill in the art and the benefit of this disclosure.

Unlike conventional spectroscopic instruments, which produce a spectrum needing further interpretation to obtain a result, the ultimate output of optical computing devices described herein is a real number that can be correlated in some manner with a contaminant in flowing atmospheric air. In addition, significant benefits may be realized by combining the outputs from two or more integrated computational elements with one another, as will be further described below, even when analyzing for a contaminant. Specifically, in some instances, significantly increased detection accuracy may be realized. Any of the methods described herein may be carried out by combining the outputs of two or more integrated computational elements with one another. The integrated computational elements whose outputs are being combined may be associated or disassociated with a characteristic of interest, display a positive or negative response when analyzing the characteristic of interest, or any combination thereof.

As alluded to above, the operational simplicity of optical computing devices makes them rugged and well suited for field or process environments, including deployment within a subterranean formation. For example, the optical computing devices described herein may analyze fluids commonly encountered in the oil and gas industry, including while deployed within a subterranean formation.

The optical computing devices disclosed herein, which are described in more detail below, can advantageously provide rapid analysis of the presence of a contaminant in flowing atmospheric air. Such flowing air may be analyzed at various stages in an oil/gas application, such as at in an air line extending from an air compressor. As used herein, the term "air line" refers to a housing, either rigid or flexible, that includes flowing air, without restriction to size and shape. Such air lines may be air ducts, plastic or metal piping, tubulars, air classification devices, and the like. Such air lines may be used during various operations, such as during pneumatic conveyance, mixing, separating, or drying of powder compositions (e.g., cements), for use in a clean room, for use in foaming treatment fluids, or any other oil and gas operation requiring an atmospheric air source.

As described above, flowing atmospheric air for use in subterranean formation operations may contain contaminants that exceed a particular acceptable limit and which contribute to contamination and poor effectiveness of downstream operations or compositions. The optical computing devices disclosed herein may provide rapid analysis of contaminants in flowing air with minimal sample prep, if any. Indeed, the optical computing devices disclosed herein may be used with already existent equipment configurations because they are small, mountable, and relatively inexpensive. They may be used in field-applications and not just in a laboratory setting. For example, optical computing devices may be mounted in an air line connected to a powder composition (e.g., cement or proppant) storage and mixing tank, and may analyze the flowing atmospheric air in the air line as it flows past the optical computing devices and detect the presence of any contaminants prior to the air reaching the powder composition. The optical computing device may also be mounted in line with an air filter or other purification equipment in the air line that receives or emits the flowing atmospheric air. One or more measurements may be taken by a particular optical computing device and/or one or more optical computing devices may be used for analyzing the flowing atmospheric air described herein.

A significant and distinct advantage of the optical computing devices disclosed herein is that they can be configured to specifically detect and/or measure a contaminant in flowing atmospheric air, thereby allowing qualitative and/or quantitative analyses of the contaminant to occur without having to undertake a time-consuming sample processing procedure. With rapid analyses capabilities on hand, the exemplary systems and methods described herein may be able to determine the percentage of a contaminant in flowing air so that an operator may determine whether the contaminant is within a particular acceptable limit range. If the contaminant is outside of the acceptable limit range (typically too high), then the particular operation may be stalled and the air line through which the flowing air is flowing cleaned or otherwise replaced and reanalyzed to ensure that the flowing air does not include unacceptable levels of contaminant(s). The use of the optical computational devices to detect the contaminant(s) in the flowing air may further be beneficial to allow for the collection and archival of information relating to contaminants of flowing air for particular operations, in conjunction with operational information, to optimize subsequent operations, and the like (e.g., to determine acceptable contaminant levels, and the like).

The optical computing devices described herein may be used to detect one or more characteristic of a contaminant of flowing atmospheric air. As used herein, the term "characteristic" refers to a chemical, mechanical, or physical property (quantitative or qualitative) of a material of interest (e.g., a contaminant). As used herein, the term "analyte" refers to a chemical component. Illustrative characteristics of a material of interest that can be monitored using the computing devices disclosed herein may include, but are not limited to, chemical composition (e.g., identity and concentration in total or of individual analytes of a contaminant), impurity content (e.g., based on known composition or amount of non-contaminants), concentration, viscosity, density, opacity, color, refractive index, liquid content, oxidation state, particle size, pH, salinity, total dissolved solids, and the like. Certain characteristics may be more desirable for use depending on the particular material of interest. For example, when the material of interest is an aqueous fluid (e.g., water vapor in flowing air), pH, total dissolved solids, and/or salinity may be desired characteristics of interest, among others. Moreover, the phrase "characteristic of interest" may be used herein to refer to a characteristic of a material of interest.

Analytes corresponding to contamination in the flowing atmospheric air of the embodiments of the present disclosure may be included therein as a result of various manufacturing processes, improper handling (e.g. air storage or compressor storage conditions), equipment malfunction or wear (e.g., from the air compressor itself, such as leakage of lubricants from an air compressor into the air line, and the like), or natural occurrence (e.g., oil contamination in atmospheric air due to exhaust from vehicles, industrial processes, and the like), and the like. Examples of analyte contaminants within flowing atmospheric air according to one or more embodiments of the present disclosure may include, but are not limited to, an aqueous liquid, an organic liquid, a carbonic acid, a gas, a dry contaminant, a biological contaminant, and any combination thereof. Combinations may include mixtures of liquid contaminants (e.g. emulsions), chemical bonds between a liquid and dry contaminant, adsorption of liquid or gas contaminants onto a dry contaminant, and the like. The term "dry contaminant" refers to a dry particulate, without being limited by size or shape or porosity.

Specific examples of analyte contaminants that may be detected using the methods of the present disclosure in flowing atmospheric air may include, but are not limited to, liquid oil, oil aerosols, oil vapor, rust atmospheric dirt, microorganisms, pipescale, and the like, and any combination thereof.

Examples of organic liquid contaminants that may be present in the flowing atmospheric air and detected as analytes using the optical computational devices described herein may include, but are not limited to, oil (e.g., alkanes, olefins, aromatic organic compounds, cyclic alkanes, paraffins, diesel fluids, mineral oils, desulfurized hydrogenated kerosenes, and the like), a glycol (e.g., diethylene glycol, ethylene glycol, propylene glycol, tetraethylene glycol, triethylene glycol, and the like), a phenol (e.g., phenol, 2-methylphenol, 2,4-dimethylphenol, 3-methylphenol, 4-methylphenol, and the like), an alkanolamine (e.g., diethanolamine, triethanolamine, triisopropanolamine, aminoethylethanolamine, triethylenetetramine, tetraethylenepentamine, hydroxyethyl diethylenetriamine, and the like), 2-butoxyethanol, benzoic acid, propanone, 2-butanone, n-propanol, ethanol, methanol, 2-butoxyethanol, derivatives thereof, isomers thereof, and any combination thereof. Examples of aqueous liquid contaminants that may be present in the flowing atmospheric air and detected as analytes using the optical computational devices described herein may include, but are not limited to, liquid water, brine (e.g., saturated or unsaturated salt water), and any combination thereof. Examples of gaseous contaminants may include, but are not limited to, water aerosols, water vapor, oil aerosols, oil vapor, and any combination thereof. As used herein, the term "vapor" refers to a substance diffused or suspended in air. The term "aerosol," as used herein, refers to a colloidal (microscopic) suspension of particles or liquid.

Dry contaminants may be any dry particulate found in the flowing atmospheric air that is not intended to be present, typically substantially none. As used herein, the term "substantially" means largely, but not necessarily wholly. Examples of potential dry contaminants may include, but are not limited to, pipescale, sand, glass, ceramic materials, polymer materials, wood, metals, clays, cements, any other dry particulate used in the oil and gas industry, and the like.

As used herein, the term "optical computing device" refers to an optical device that is configured to receive an input of electromagnetic radiation from a substance or sample of the substance, and produce an output of electromagnetic radiation from a processing element arranged within the optical computing device. As used herein, the term "electromagnetic radiation" refers to radio waves, microwave radiation, infrared and near-infrared radiation, visible light, ultraviolet light, X-ray radiation and gamma ray radiation. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one characteristic of the contaminant being measured or monitored. The output of electromagnetic radiation from the processing element can be reflected electromagnetic radiation, transmitted electromagnetic radiation, and/or dispersed electromagnetic radiation. Whether reflected, transmitted, (e.g., fluorescence, blackbody, or phosphorescence), and/or dispersed, electromagnetic radiation is analyzed by the detector and may be dictated by the structural parameters of the optical computing device as well as other considerations known to those skilled in the art. In some embodiments, which may be preferred to detect the contaminants described herein, emission and/or scattering by the contaminant, for example via fluorescence, luminescence, Raman scattering, Brillion scattering, and/or Raleigh scattering, can be monitored by the optical computing devices.

As used herein, the term "optically interact" or variations thereof refer to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a contaminant in flowing atmospheric air.

As an example, electromagnetic radiation (e.g., in the form of near-infrared light) may be optically interacted with flowing atmospheric air and may be optically interacted with an ICE. The telectromagnetic radiation may optically interact with the flowing atmospheric air and the ICE in any order without limitation (air first, ICE first, or simultaneously). The electromagnetic radiation that has optically interacted with both the ICE and the flowing atmospheric air may then be detected by a detector configured to generate an output signal corresponding to a contaminant in the flowing atmospheric air.

The exemplary systems and methods described herein include at least one optical computing device configured to measure at least one characteristic of a contaminant in flowing atmospheric air, such as in an air line extending from an air compressor. In some embodiments, the optical computing devices suitable for use in the exemplary systems and methods described herein may be mobile or portable.

An optical computing device may include an electromagnetic radiation source, at least one processing element (e.g., an integrated computational element), and at least one detector arranged to receive optically interacted light from the at least one processing element. However, in at least one embodiment, the electromagnetic radiation source may be omitted and instead the electromagnetic radiation may be derived from the contaminant itself. In some embodiments, the exemplary optical computing devices may be specifically configured for detecting, analyzing, and quantitatively measuring a particular characteristic of the contaminant. In other embodiments, the optical computing devices may be general purpose optical devices, with post-acquisition processing (e.g., through computer means) being used to specifically detect the characteristic of interest.

The presently described optical computing devices combine the advantage of the power, precision, and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics of interest, including contaminants in flowing atmospheric air. As a result, interfering signals are discriminated from those of interest by appropriate configuration of the optical computing devices, such that the optical computing devices provide a rapid response regarding the characteristic of interest as based on the detected output. In some embodiments, the detected output can be converted into a voltage that is distinctive of the magnitude of the characteristic of interest. The foregoing advantages and others make the optical computing devices particularly well suited for field use.

The optical computing devices can be configured to detect not only the composition and concentrations of an analyte in flowing atmospheric air, but they can also be configured to determine physical properties and other characteristics of the contaminant as well, based on their analysis of the electromagnetic radiation received from the contaminant. For example, the optical computing devices can be configured to determine the concentration of an analyte and correlate the determined concentration to a characteristic of the contaminant by using suitable processing means. As will be appreciated, the optical computing devices may be configured to detect as many characteristics as desired for a given contaminant. All that is required to accomplish the monitoring of multiple characteristics of interest is the incorporation of suitable processing and detection means within the optical computing device for each characteristic of interest (e.g., the concentration of an analyte, and the like). In some embodiments, the properties of the contaminant may be determined using a combination of characteristics of interest (e.g., a linear, non-linear, logarithmic, and/or exponential combination). Accordingly, the more characteristics that are detected and analyzed using the optical computing devices, the more accurately the properties of the contaminant will be determined. For example, properties of a contaminant that may be determined using optical computing devices described herein may include, but are not limited to, the absolute concentration of an analyte, the relative ratios of two or more analytes, the presence or absence of an analyte, and the like, and any combination thereof.

The optical computing devices described herein utilize electromagnetic radiation to perform calculations, as opposed to the hardwired circuits of conventional electronic processors. When electromagnetic radiation interacts with a material of interest (e.g., a contaminant), unique physical and chemical information about the material of interest may be encoded in the electromagnetic radiation that is reflected from, transmitted through, or radiated from the material of interest. The optical computing devices described herein are capable of extracting the information of the spectral fingerprint of multiple characteristics of a material of interest, and converting that information into a detectable output regarding the overall properties of the monitored material of interest. That is, through suitable configurations of the optical computing devices, electromagnetic radiation associated with characteristics of interest can be separated from electromagnetic radiation associated with all other components of the material of interest in order to estimate the properties of the monitored substance (e.g., a contaminant) in real-time or near real-time.

The processing elements used in the exemplary optical computing devices described herein may be characterized as integrated computational elements (ICE). Each ICE is capable of distinguishing electromagnetic radiation related to the characteristic of interest from electromagnetic radiation related to other components of flowing atmospheric air. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, $SiO_x$, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest using a conventional spectroscopic instrument. The spectrum of interest of a given characteristic of interest typically includes any number of different wavelengths. It should be understood that the exemplary ICE 100 in FIG. 1 does not in fact represent any particular characteristic of interest, but is provided for purposes of illustration only. Consequently, the number of layers 102, 104 and their relative thicknesses, as shown in FIG. 1, bear no correlation to any particular characteristic of interest. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the materials to the monitored substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 may contain a corresponding vessel (not shown), which houses the gases or liquids. Exemplary variations of the ICE 100 may also include holographic optical elements, gratings, piezoelectric, light pipe, digital light pipe (DLP), molecular factor devices, variable optical attenuators, and/or acousto-optic elements, for example, that can create transmission, reflection, and/or absorptive properties of a material of interest or contaminant.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic of interest.

Figure 2:
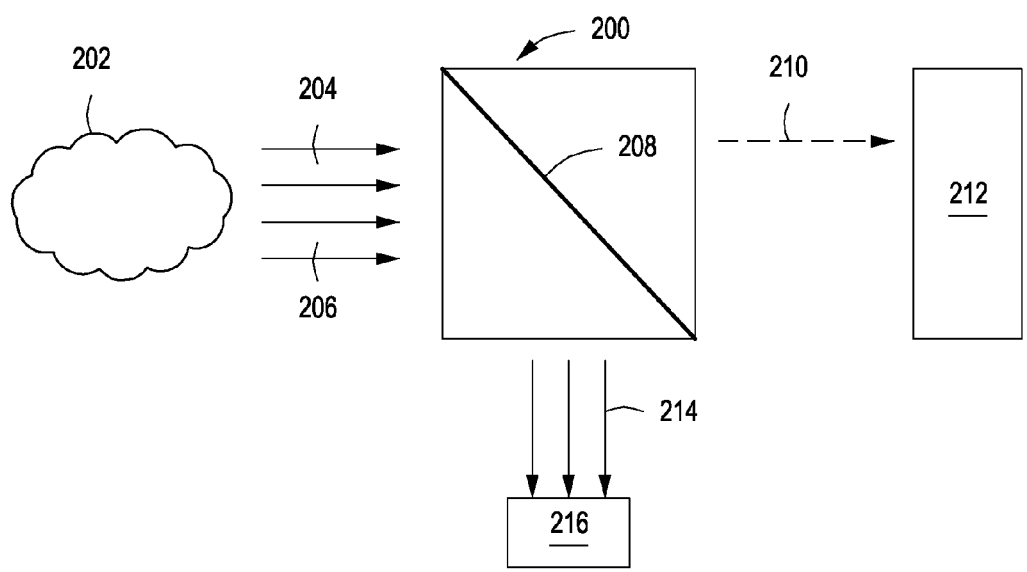
FIG. 2 illustrates a block diagram non-mechanistically illustrating how an optical computing device distinguishes electromagnetic radiation related to a characteristic of interest from other electromagnetic radiation, according to one or more embodiments described herein.

Referring now to FIG. 2, illustrated is a block diagram that non-mechanistically illustrates how an optical computing device 200 is able to distinguish electromagnetic radiation related to a characteristic of interest from other electromagnetic radiation. As shown in FIG. 2, after being illuminated with incident electromagnetic radiation, flowing atmospheric air 202 produces an output of electromagnetic radiation (e.g., sample-interacted light), some of which is electromagnetic radiation 204 corresponding to the characteristic of interest and some of which is background electromagnetic radiation 206 corresponding to other characteristics of the flowing atmospheric air 202. In some embodiments, the flowing atmospheric air 202 may include one or more characteristics of interest that may correspond to the one or more analytes of a contaminant in the flowing atmospheric air 202.

Although not specifically shown, one or more processing elements may be employed in the optical computing device 200 in order to restrict the optical wavelengths and/or bandwidths of the system and thereby eliminate unwanted electromagnetic radiation existing in wavelength regions that have no importance. Such processing elements can be located anywhere along the optical train, but are typically employed directly after a light source, which provides the initial electromagnetic radiation.

The beams of electromagnetic radiation 204, 206 impinge upon the optical computing device 200, which contains an exemplary ICE 208 therein. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to the characteristic of interest of a contaminant in the flowing atmospheric air 202, may be conveyed to a detector 212 for analysis and quantification. In some embodiments, the detector 212 is configured to produce an output signal in the form of a voltage that corresponds to the particular characteristic of the contaminant in the flowing atmospheric air 202. In at least one embodiment, the signal produced by the detector 212 and the characteristic of the contaminant of the flowing atmospheric air 202 (e.g., concentration of an analyte of the contaminant) may be directly proportional. In other embodiments, the relationship may be a polynomial function, an exponential function, and/or a logarithmic function. The reflected optically interacted light 214, which may be related to other characteristics of the contaminant in the flowing atmospheric air 202, can be directed away from detector 212. In alternative configurations, the ICE 208 may be configured such that the reflected optically interacted light 214 can be related to the characteristic of the contaminant, and the transmitted optically interacted light 210 can be related to other characteristics in the flowing atmospheric air 202.

In some embodiments, a second detector 216 can be present and arranged to detect the reflected optically interacted light 214. In other embodiments, the second detector 216 may be arranged to detect the electromagnetic radiation 204, 206 derived from the flowing atmospheric air 202 or electromagnetic radiation directed toward or before the flowing atmospheric air 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to two or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to the detector 212.

The characteristic(s) of interest being analyzed using the optical computing device 200 can be further processed and/or analyzed computationally to provide additional characterization information about the flowing atmospheric air 202, the contaminant therein, or an analyte thereof. In some embodiments, the identification and concentration of one or more analytes of a contaminant in the flowing atmospheric air 202 can be used to predict certain physical characteristics of the contaminant in the flowing atmospheric air 202. For example, the bulk characteristics of contaminants in the flowing atmospheric air 202 can be estimated. By so doing, the amount of the contaminant in the flowing atmospheric air 202 may be evaluated to ensure that it is present within acceptable limits. The acceptable limits of contaminants in the flowing atmospheric air 202 are highly dependent on the type of contaminant (e.g., the phase such as liquid, gaseous, or dry particulate, the chemical makeup, and the like), the type of operation the flowing atmospheric air 202 is expected to be used during, and the like. For example, if the flowing atmospheric air 202 is used to dry or mix a cement composition, the presence of a certain contaminant in a certain concentration may have varying effects on the hydration rate, for example, depending on the type of cement in the composition, the temperature of the downhole operation, the downhole environment (e.g., if it is a salt formation, for example), among other variables. One of skill in the art, with the benefit of this disclosure, can determine acceptable limits of particular contaminants in particular flowing atmospheric air based on such factors. Accordingly, where one or more computing devices 200 is used according to the methods herein to detect a characteristic of interest, different acceptable limit ranges may apply to one or more characteristics of one or more contaminants therein.

In some embodiments, the magnitude of the characteristic of interest determined using the optical computing device 200 can be fed into an algorithm operating under computer control. The algorithm may be configured to determine whether the contaminant in the flowing atmospheric air 202 is in programmed acceptable limits, which may be narrowed depending on a particular operation. In some embodiments, the algorithm can produce an output that is readable by an operator who can manually take appropriate action, if needed, based upon the reported output. For example, if the flowing atmospheric air 202 comprises an amount of contaminant that is not within the acceptable limits, the operator may take corrective action to bring the amount of contamination within acceptable limits, for example, altering the source of the flowing atmospheric air, adding additional chemicals to counteract the contaminant(s), and the like. These may be referred to collectively as "modifying the flowing atmospheric air." Moreover, corrective action to bring the amount of contamination within acceptable limits may include, for example, cleaning the air line, substituting equipment (e.g., compressor units, compressor lines, storage tanks upstream or downstream of the flowing atmospheric air), and the like. These may be referred to collectively as "modifying the external conditions relative to the flowing atmospheric air." In some embodiments, both modification of the flowing atmospheric air and modification of the external conditions relative to the flowing atmospheric air may be utilized. In some embodiments, the algorithm may direct the operator as to how to take such corrective action (e.g., how to bring the contaminants in the flowing atmospheric air 202 within acceptable limits).

In other embodiments, the algorithm can take proactive process control. For example, the algorithm may be used to determine whether to stop operations or automatically take corrective action (e.g., by switching to another atmospheric air source automatically) based on a determination of the composition and concentration of any contaminants in the flowing atmospheric air. It is to be recognized that the algorithm (e.g., an artificial neural network) can be trained using samples of predetermined characteristics of interest, and thereby generating a virtual library. As the virtual library available to the artificial neural network becomes larger, the neural network can become more capable of accurately predicting the characteristic of interest corresponding to a contaminant or analyte thereof. Furthermore, with sufficient training, the artificial neural network can more accurately predict the characteristics of the contaminant, even in the presence of unknown analytes.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system may also allow remote monitoring to take place. Automated control with a long-range communication system can further facilitate the performance of remote job operations. In particular, an artificial neural network can be used in some embodiments to facilitate the performance of remote job operations. That is, remote job operations may be conducted automatically in some embodiments. In other embodiments, however, remote job operations can occur under direct operator control, where the operator is not at the job site (e.g., via wireless technology).

Referring now to FIG. 3, illustrated is an exemplary system 300 for monitoring flowing atmospheric air 302, according to one or more embodiments. In the illustrated embodiment, the flowing atmospheric air 302 may be flowing within an exemplary flow path 304. The exemplary flow path 304 may be, for example, an air line extending from an air compressor. The flowing atmospheric air 302 present within the flow path 304 may be flowing in the general direction indicated by the arrows A (i.e., upstream to downstream). As will be appreciated by one of skill in the art, however, a flow path 304 may be in any direction, including a circular direction, without departing from the scope of the present disclosure.

The system 300 may include at least one optical computing device 306, which may be similar in some respects to the optical computing device 200 of FIG. 2. While not shown, the device 306 may be housed within a casing or housing configured to substantially protect the internal components of the device 306 from damage or contamination from the external environment. The housing may operate to mechanically couple or otherwise place in communication the device 306 to the flow path 304 with, for example, mechanical fasteners, brazing or welding techniques, adhesives, magnets, combinations thereof or the like.

As described in greater detail below, the optical computing device 306 may be useful in determining a particular characteristic of a contaminant the flowing atmospheric air 302 within the flow path 304, such as determining a concentration of an analyte present within the contaminant in the flowing atmospheric air 302. In some embodiments, the device 306 may include an electromagnetic radiation source 308 configured to emit or otherwise generate electromagnetic radiation 310. The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-Ray source, a gamma ray source, combinations thereof, or the like. In some embodiments, a lens 312 may be configured to collect or otherwise receive the electromagnetic radiation 310 and direct a beam 314 of electromagnetic radiation 310 toward the flowing atmospheric air 302. The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 312 may be omitted from the device 306 and the electromagnetic radiation 310 may instead be conveyed toward the flowing atmospheric air 302 directly from the electromagnetic radiation source 308.

In one or more embodiments, the device 306 may also include a sampling window 316 arranged adjacent to or otherwise in contact with the flowing atmospheric air 302 for detection purposes. The sampling window 316 may be composed from a variety of transparent, rigid or semi-rigid materials that are configured to allow transmission of the electromagnetic radiation 310 therethrough. For example, the sampling window 316 may be made composed of, but is not limited to, glasses, plastics, semi-conductors, crystalline materials, polycrystalline materials, hot or cold-pressed powders, combinations thereof, or the like.

After passing through the sampling window 316, the electromagnetic radiation 310 impinges upon and optically interacts with the contaminants and analytes thereof in the flowing atmospheric air 302. It is understood that in some embodiments, the electromagnetic radiation 310 may impinge upon and optically interact with the flowing atmospheric air 302 itself to determine the presence of any contaminant, without departing from the scope of the present disclosure. As a result, optically interacted radiation 318 is generated by and reflected from the contaminants in the flowing atmospheric air 302. Those skilled in the art, however, will readily recognize that alternative variations of the device 306 may allow the optically interacted radiation 318 to be generated by being transmitted, scattered, diffracted, absorbed, emitted, or re-radiated by and/or from the contaminants in the flowing atmospheric air 302, or one or more analytes of the contaminant present within the flowing atmospheric air 302, without departing from the scope of the disclosure.

The optically interacted radiation 318 generated by the interaction with the contaminants in the flowing atmospheric air 302 may be directed to or otherwise received by an ICE 320 arranged within the device 306. The ICE 320 may be a spectral component substantially similar to the ICE 100 described above with reference to FIG. 1. Accordingly, in operation the ICE 320 may be configured to receive the optically interacted radiation 318 and produce modified electromagnetic radiation 322 corresponding to a particular characteristic of interest of the contaminant in the flowing atmospheric air 302. In particular, the modified electromagnetic radiation 322 is electromagnetic radiation that has optically interacted with the ICE 320, whereby an approximate mimicking of the regression vector corresponding to the characteristic of interest is obtained. In some embodiments, the characteristic of interest corresponds to a liquid component of the particular analyte thereof in the flowing atmospheric air 302.

Figure 3:
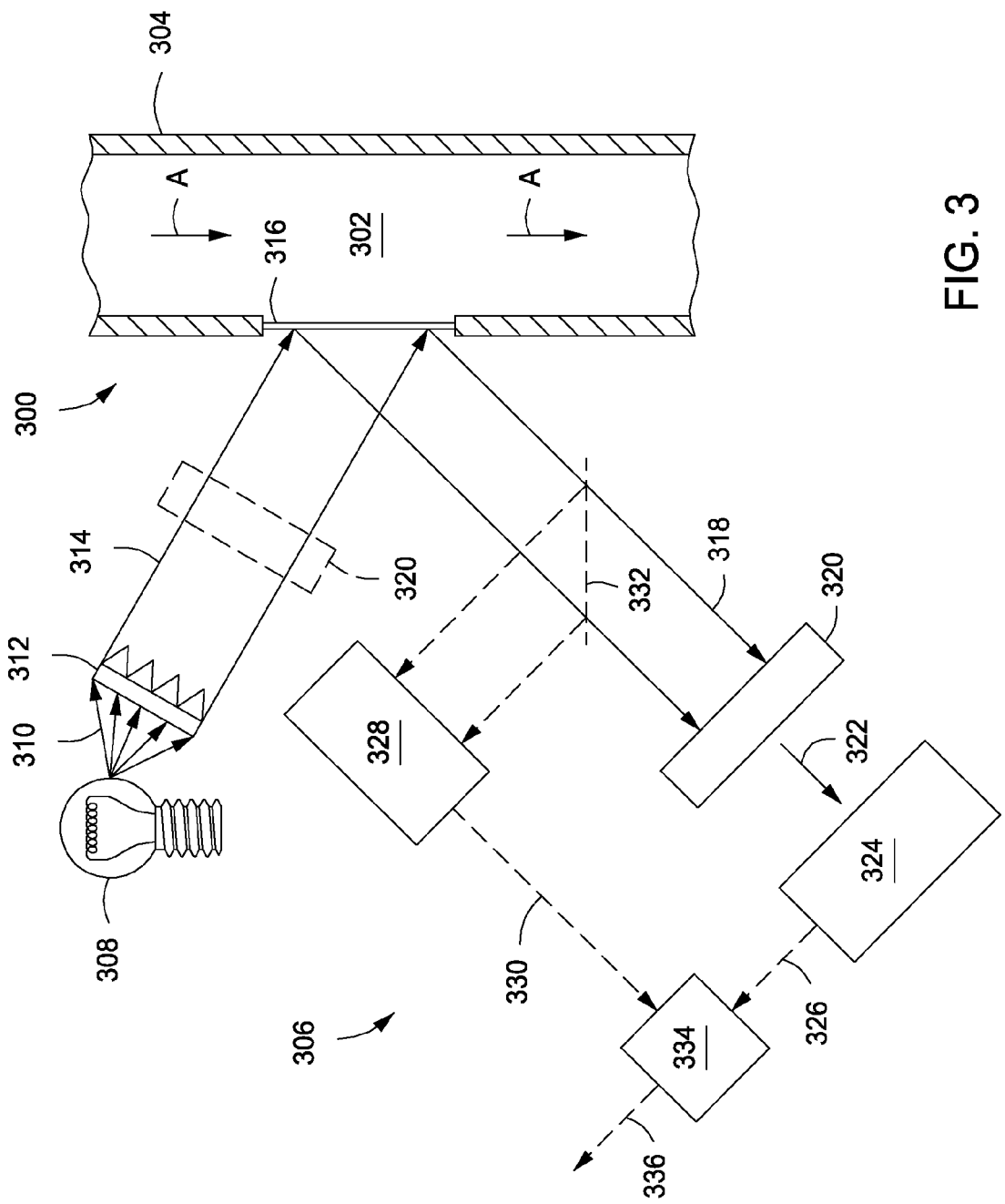
FIG. 3 illustrates an exemplary system for detecting a contaminant in flowing atmospheric air, according to one or more embodiments.

It should be noted that, while FIG. 3 depicts the ICE 320 as receiving optically interacted radiation 318 from the contaminant in flowing atmospheric air 302, the ICE 320 may be arranged at any point along the optical train of the device 306, without departing from the scope of the disclosure. For example, in one or more embodiments, the ICE 320 (as shown in dashed) may be arranged within the optical train prior to the sampling window 316 and equally obtain substantially the same results. In other embodiments, the sampling window 316 may serve a dual purpose as both a transmission window and the ICE 320 (i.e., a spectral component). In yet other embodiments, the ICE 320 may generate the modified electromagnetic radiation 322 through reflection, instead of transmission therethrough.

Moreover, while only one ICE 320 is shown in the device 306, embodiments are contemplated herein which include the use of at least two ICE 320 components in the device 306 configured to cooperatively determine the characteristic of interest in the flowing atmospheric air 302. For example, two or more ICE 320 may be arranged in series or parallel within the device 306 and configured to receive the optically interacted radiation 318 and thereby enhance sensitivities and detector limits of the device 306. In other embodiments, two or more ICE 320 may be arranged on a movable assembly, such as a rotating disc or an oscillating linear array, which moves such that the individual ICE 320 components are able to be exposed to or otherwise optically interact with electromagnetic radiation 310 for a distinct brief period of time. The two or more ICE 320 components in any of these embodiments may be configured to be either associated or disassociated with the characteristic of interest in the flowing atmospheric air 302. In other embodiments, the two or more ICE 320 components may be configured to be positively or negatively correlated with the characteristic of interest.

In some embodiments, it may be desirable to monitor more than one characteristic of interest at a time using the device 306. In such embodiments, various configurations for multiple ICE 320 components can be used, where each ICE 320 component is configured to detect a particular and/or distinct characteristic of interest corresponding, for example, a characteristic of a contaminant present in the flowing atmospheric air 302. In some embodiments, the characteristic of interest can be analyzed sequentially using multiple ICE 320 components that are provided a single beam of optically interacted radiation 318 being reflected from or transmitted through the flowing atmospheric air 302 to detect the contaminant. In some embodiments, as described in more detail below, multiple ICE 320 components can be arranged on a rotating disc, where the individual ICE 320 components are only exposed to the beam of optically interacted radiation 318 for a short time. Advantages of this approach can include the ability to analyze multiple characteristics of interest of a contaminant (or multiple types of contaminants) within the flowing atmospheric air 302 using a single device 306 and the opportunity to assay additional characteristics simply by adding additional ICE 320 components corresponding to those additional characteristics or corresponding to different types of contaminants.

In other embodiments, multiple devices 306 can be placed at a single location along the flow path 304, where each device 306 contains a unique ICE 320 that is configured to detect a particular characteristic of interest. In such embodiments, a beam splitter can divert a portion of the optically interacted radiation 318 being reflected by, emitted from, or transmitted through the flowing atmospheric air 302 and into each device 306. Each device 306, in turn, can be coupled to a corresponding detector or detector array that is configured to detect and analyze an output of electromagnetic radiation from the respective device 306. Parallel configurations of optical computing devices can be particularly beneficial for applications that require low power inputs and/or no moving parts.

Figure 5:
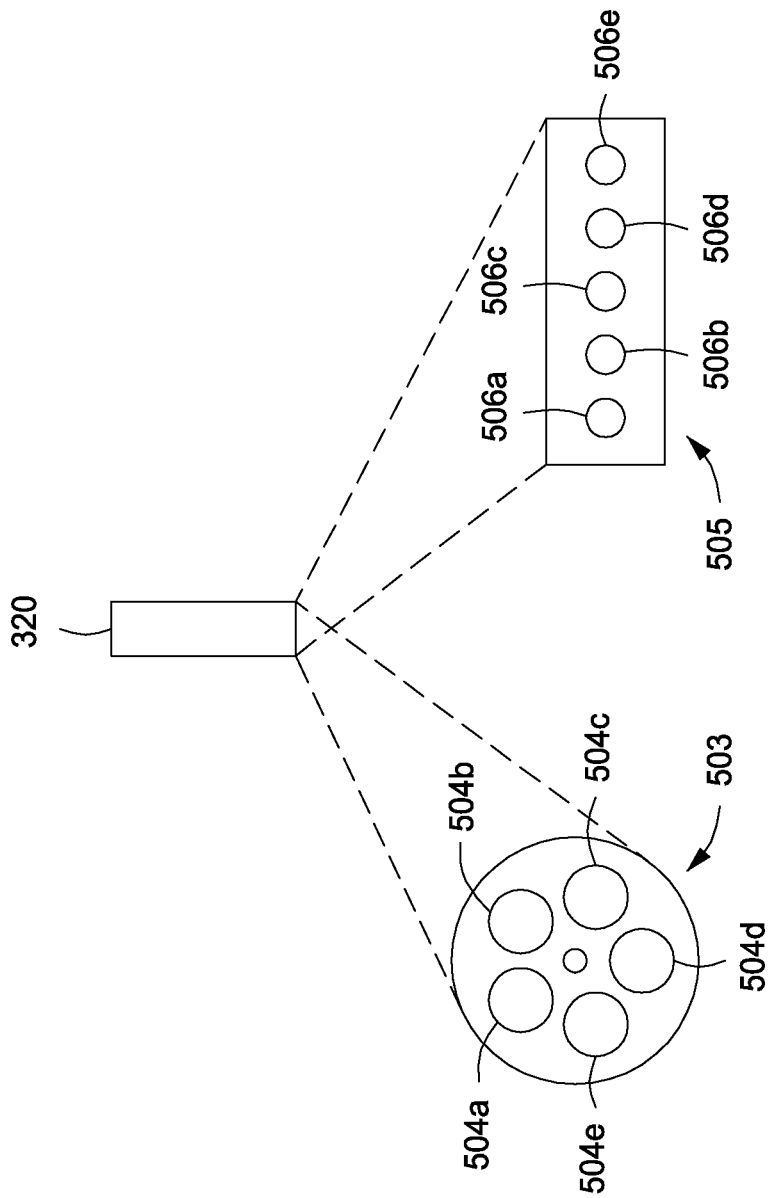
FIG. 5 illustrates a schematic of illustrative arrays of integrated computational elements.

In some embodiments, the single ICE 320 may be replaced by an array of integrated computational elements, as illustratively depicted in FIG. 5. By moving the integrated computational elements of the depicted arrays with respect to the electromagnetic radiation, different integrated computational elements may be exposed to the electromagnetic radiation over time. In some embodiments, the array may comprise rotating disc 503 containing integrated computational elements 504a-504e thereon. In other embodiments, the array may comprise movable assembly 505 having integrated computational elements 506a-506e thereon, in which movable assembly 505 is shifted or reciprocated laterally over the course of time to expose integrated computational elements 506a-506e to electromagnetic radiation. It is to be recognized that although the arrays of FIG. 5 have depicted five integrated computational elements in the array, any number may be present.

Referring back to FIG. 3, with reference to FIG. 5, those skilled in the art will appreciate that any of the foregoing configurations can further be used in combination with a series configuration in any of the present embodiments. For example, two devices 306 may be arranged in series, such as being located on or within a movable housing configured to perform an analysis at a single location in the flow path 304. Likewise, multiple detection stations, each containing devices 306 in parallel, can be placed in series for performing a similar analysis.

The modified electromagnetic radiation 322 generated by the ICE 320 may subsequently be conveyed to a detector 324 for quantification of the signal. The detector 324 may be any device capable of detecting electromagnetic radiation, and may be generally characterized as an optical transducer. In some embodiments, the detector 324 may be, but is not limited to, a thermal detector such as a thermopile or photoacoustic detector, a semiconductor detector, a piezo-electric detector, a charge coupled device (CCD) detector, a video or array detector, a split detector, a quad detector, a photon detector (such as a photomultiplier tube), photodiodes, combinations thereof, or the like, or other detectors known to those skilled in the art.

In some embodiments, the detector 324 may be configured to produce an output signal 326 in real-time or near real-time in the form of a voltage (or current) that corresponds to the particular characteristic of interest of a contaminant in the flowing atmospheric air 302. The voltage returned by the detector 324 is essentially the dot product of the optical interaction of the optically interacted radiation 318 with the respective ICE 320 as a function of the concentration of the characteristic of interest. As such, the output signal 326 produced by the detector 324 and the concentration of the characteristic of interest may be related, for example, directly proportional. In other embodiments, however, the relationship may correspond to a polynomial function, an exponential function, a logarithmic function, and/or a combination thereof.

In some embodiments, the device 306 may include a second detector 328, which may be similar to the first detector 324 in that it may be any device capable of detecting electromagnetic radiation. Similar to the second detector 216 of FIG. 2, the second detector 328 of FIG. 3 may be used to detect radiating deviations stemming from the electromagnetic radiation source 308. Undesirable radiating deviations can occur in the intensity of the electromagnetic radiation 310 due to a wide variety of reasons and potentially causing various negative effects on the output of the device 306. These negative effects can be particularly detrimental for measurements taken over a period of time. In some embodiments, radiating deviations can occur as a result of a build-up of film or material on the sampling window 316, which has the effect of reducing the amount and quality of light ultimately reaching the first detector 324. Without proper compensation, such radiating deviations could result in false readings and the output signal 326 would no longer be primarily or accurately related to the characteristic of interest.

To compensate for these types of undesirable effects, the second detector 328 may be configured to generate a compensating signal 330 generally indicative of the radiating deviations of the electromagnetic radiation source 308, and thereby normalize the output signal 326 generated by the first detector 324. As illustrated, the second detector 328 may be configured to receive a portion of the optically interacted radiation 318 via a beam splitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure.

In some applications, the output signal 326 and the compensating signal 330 may be conveyed to or otherwise received by a signal processor 334 communicably coupled to both the detectors 324, 328. The signal processor 334 may be a computer including a non-transitory machine-readable medium, and may be configured to computationally combine the compensating signal 330 with the output signal 326 in order to normalize the output signal 326 in view of any radiating deviations detected by the second detector 328 and produce a resulting output signal 336. In some embodiments, computationally combining the output and compensating signals 326, 330 may entail computing a ratio of the two signals 326, 330. For example, the concentration or magnitude of each characteristic of interest determined using the optical computing device 306 can be fed into an algorithm run by the signal processor 334.

In real-time or near real-time, the signal processor 334 may be configured to provide the resulting output signal 336 corresponding to a concentration of the characteristic of interest in the flowing atmospheric air 302. The resulting output signal 336 may be readable by an operator who can consider the results and make proper adjustments or take appropriate action, if needed, based upon the measured concentrations of contaminant(s) in the flowing atmospheric air 302. In some embodiments, the resulting signal output 336 may be conveyed, either wired or wirelessly, to an operator for consideration. In other embodiments, the resulting output signal 336 of the characteristic of interest may be recognized by the signal processor 334 as being within or without an acceptable limit range for the flowing atmospheric air 302 or for a particular operation and may alert the operator of an out of range reading so appropriate corrective action may be taken, or otherwise autonomously undertake the appropriate corrective action such that the resulting output signal 336 returns to a value within the predetermined or preprogrammed range of suitable operation.

Figure 4:
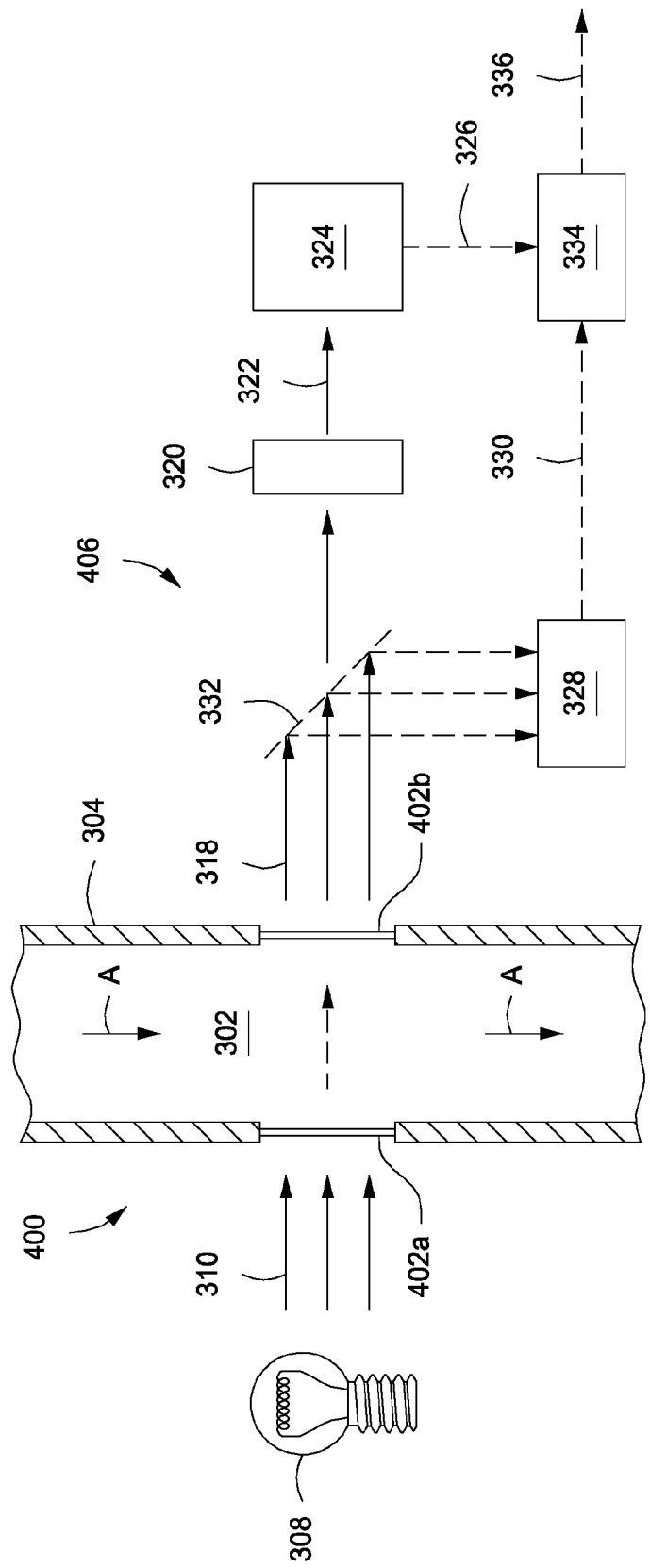
FIG. 4 illustrates another exemplary system for detecting a contaminant in flowing atmospheric air, according to one or more embodiments.

Referring now to FIG. 4, illustrated is another exemplary system 400 including at least one optical computing device 406 for monitoring flowing atmospheric air 302, according to one or more embodiments. The exemplary system 400 and optical computing device 406 may be similar in some respects to the system 300 and optical computing device 306 of FIG. 3, and therefore may be best understood with reference thereto where like numerals indicate like elements that will not be described again. The optical computing device 406 may be configured to determine the concentration of a characteristic of interest in the flowing atmospheric air 302 as contained within a flow path 304. Unlike the system 300 of FIG. 3, however, the optical computing device 406 of FIG. 4 may be configured to transmit the electromagnetic radiation 310 through the flowing atmospheric air 302 in the flow path 304 via a first sampling window 402a and a second sampling window 402b arranged radially-opposite the first sampling window 402a. The first and second sampling windows 402a,b may be similar to the sampling window 316 described above with reference to FIG. 3 and therefore will not be described again.

As the electromagnetic radiation 310 passes through the flowing atmospheric air 302 via the first and second sampling windows 402a,b, it optically interacts with the flowing atmospheric air 302 and optically interacted radiation 318 is subsequently directed to or otherwise received by the ICE 320 as arranged within the device 406. It is again noted that, while FIG. 4 depicts the ICE 320 as receiving the optically interacted radiation 318 as transmitted through the sampling windows 402a,b, the ICE 320 may equally be arranged at any point along the optical train of the device 406, without departing from the scope of the disclosure. For example, in one or more embodiments, the ICE 320 may be arranged within the optical train prior to the first sampling window 402a and equally obtain substantially the same results. In yet other embodiments, the ICE 320 may generate the modified electromagnetic radiation 322 through reflection, instead of transmission therethrough. Moreover, as with the device 306 of FIG. 3, embodiments are contemplated herein which include the use of at least two ICE components in the device 406 configured to cooperatively determine the characteristic of interest in the flowing atmospheric air 302.

The modified electromagnetic radiation 322 generated by the ICE 320 is subsequently conveyed to the detector 324 for quantification of the signal and generation of the output signal 326 which corresponds to the particular characteristic of interest in the flowing atmospheric air 302. The device 406 may also include the second detector 328 for detecting radiating deviations stemming from the electromagnetic radiation source 308. As illustrated, the second detector 328 may be configured to receive a portion of the optically interacted radiation 318 via the beam splitter 332 in order to detect the radiating deviations. The output signal 326 and the compensating signal 330 may then be conveyed to or otherwise received by the signal processor 334 which may computationally combine the two signals 330, 326 and provide in real-time or near real-time the resulting output signal 336 corresponding to the concentration of the characteristic of interest in the flowing atmospheric air 302.

Those skilled in the art will readily recognize that, in one or more embodiments, electromagnetic radiation may be derived from the flowing atmospheric air 302 or the contaminant itself, and otherwise derived independent of any electromagnetic radiation source 308 (FIGS. 3 and 4). For example, various substances naturally radiate electromagnetic radiation that is able to optically interact with the ICE 320 (FIGS. 2 and 3). In some embodiments, for example, the flowing atmospheric air 302 or contaminant being analyzed may be a blackbody radiating substance configured to radiate heat that may optically interact with the ICE 320. In other embodiments, the flowing atmospheric air 302 or contaminant may be radioactive or chemo-luminescent and, therefore, radiate electromagnetic radiation that is able to optically interact with the ICE 320. In yet other embodiments, the electromagnetic radiation may be induced from the flowing atmospheric air 302 or contaminant by being acted upon mechanically, magnetically, electrically, combinations thereof, or the like. For instance, in at least one embodiment, a voltage may be placed across the flowing atmospheric air 302 in order to induce the electromagnetic radiation. As a result, embodiments are contemplated herein where the electromagnetic radiation source 308 may be omitted from the optical computing devices described herein.

Figure 6:
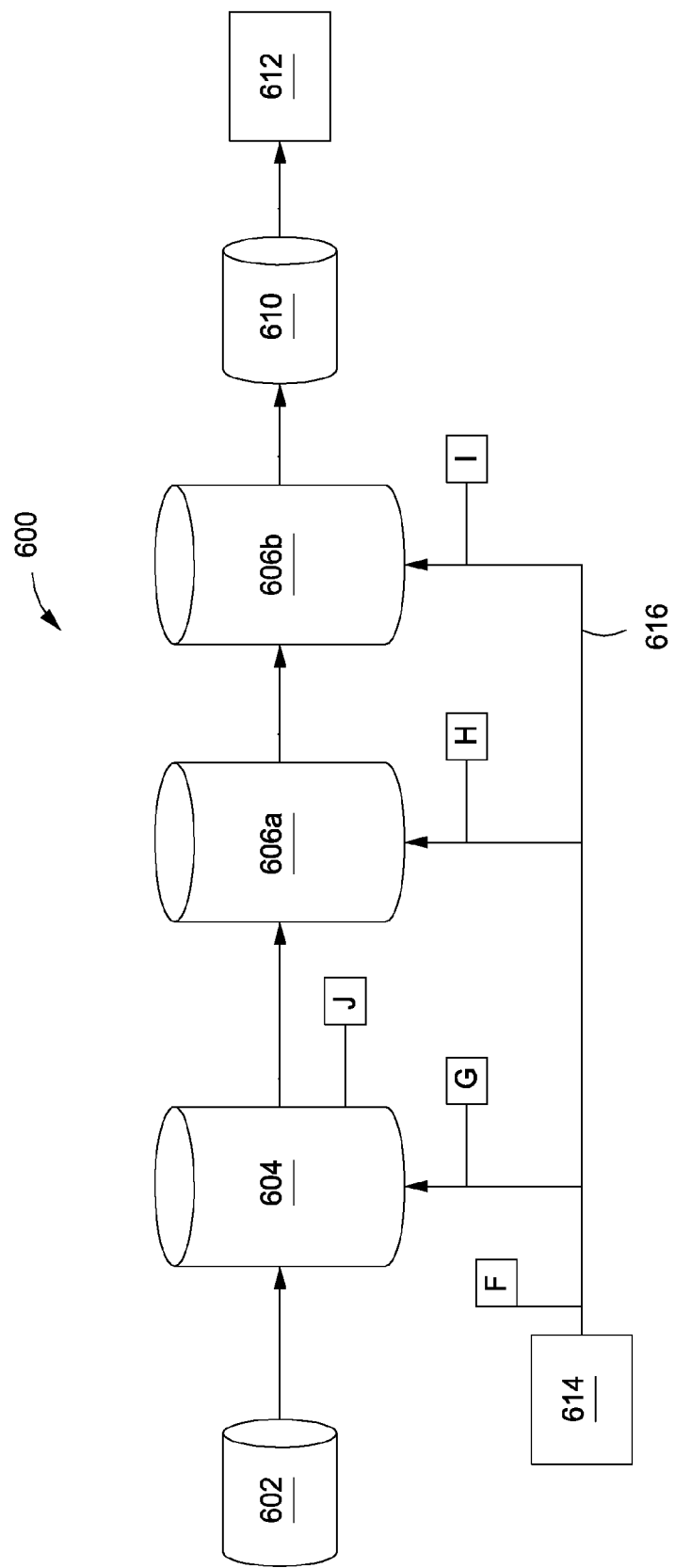
FIG. 6 illustrates a powder composition process flow that may utilize one or more exemplary systems for detecting a contaminant in flowing atmospheric air used as part of the process flow.

Referring now to FIG. 6, illustrated is a flow chart depicting a bulk powder composition (e.g., proppant, cement, gravel, and the like) process flow 600 for use in a subterranean formation operation that may utilize one or more exemplary systems comprising the optical computing devices described herein in air lines connected therebetween. The optical computing devices that may be used in the process flow 600 may be substantially similar to the optical computing device 306 of FIG. 3 and/or the optical computing device 406 of FIG. 4, and therefore will not be described again in detail. A powder composition (not shown) may be pneumatically conveyed between a transport vessel 602, a storage tank 604, a first blend tank 606a, a second blend tank 606b, a job transport tank 610, and a jobsite structure 612.

It will be appreciated that the specific configuration of the process flow 600 depicted in FIG. 6 is merely illustrative and other configurations may be adopted in accordance with the embodiments described herein. For example, although two blend tanks 606a,b are depicted in FIG. 6, it will be appreciated that a single blend tank may be included in the process flow 600 or more than two blend tanks may be included in the process flow 600, depending on the specific needs of a particular powder composition or operation, without departing from the scope of the present disclosure. Moreover, in some embodiments, the storage tank 604 may be omitted and the powder composition may be conveyed directly from the transport vessel 602 to one or more blend tanks 606.

An air supply 614 (e.g., a compressor) may be connected via one or more air lines 616 carrying flowing atmospheric air and used to dry or otherwise aerate or mix the powder composition in one or more of the storage tank 604 and/or the first or second blend tanks 606a,b. One or more of the optical computing devices described herein may be used to monitor contaminants that are within the flowing atmospheric air in the air lines 616 from the air supply 614 at any location, such as those depicted at F, G, H, and I, in accordance with the embodiments herein.

Although the air line 616 is illustrated as being in-line and connecting the air supply 614 and each of the storage tank 604 and blend tanks 606a,b, it will be appreciated by one of skill in the art that the air line 616 may connect to only one of the storage tank 604 or blend tanks 606a, b, without departing from the scope of the present disclosure. Similarly, it is not necessary that a single air supply 614 supply air to more than one of the storage tank 604 or blend tanks 606a, b; rather, a single air supply 614 may be connected to each tank. Furthermore, where a single air line 616 is used to supply more than one of the storage tank 604 or blend tanks 606a, b, the air line 616 may comprise a valve (e.g., a two-way valve) at any location along the air line 616 to control the airflow toward a particular tank.

Other configurations of the process flow 600 may also be suitable, without departing from the scope of the present disclosure. For example, one or more optical computing devices at locations F-J of the process flow 600 may be in any combination. That is, any single location may comprise an optical computing device and any combination of one or more of locations F-J may comprise an optical computing device. Moreover, any other location capable of housing an optical computing device as described herein for monitoring a contaminant in the flowing atmospheric air at a location along the process flow 600. In some embodiments, the one or more optical computing devices located along the process flow 600 may be capable of detecting the same characteristic of interest or different characteristics of interest and may further be designed to provide an output that may be read by an algorithm capable of determining whether the contaminant is within an acceptable limit range, which may vary at different locations along the process flow 600.

In some embodiments, the methods described herein may comprise optically interacting electromagnetic radiation with flowing atmospheric air and a first integrated computational element (ICE), the first ICE being configured to detect a contaminant in a flowing atmospheric air; receiving the electromagnetic radiation with a detector; and generating an output signal corresponding to a characteristic of the contaminant in the flowing atmospheric air. The characteristic of the contaminant may be any characteristic or analyte of the contaminant, such as composition or concentration characteristics. In one exemplary embodiment, the characteristic of the contaminant detected may be the concentration of the contaminant and further comprising determining if the concentration of the contaminant is within an acceptable limit range in the flowing atmospheric air, as is described herein.

In other embodiments, the methods described herein may comprise optically interacting electromagnetic radiation with flowing atmospheric air and a first integrated computational element (ICE), the first ICE configured to detect a first contaminant in the flowing atmospheric air; optically interacting electromagnetic radiation with the flowing atmospheric air and at least a second ICE, the second ICE configured to detect a second contaminant in the flowing atmospheric air; receiving the electromagnetic radiation with at least one detector; and generating a first output signal corresponding to a characteristic of the first contaminant in the flowing atmospheric air and a second output signal corresponding to a second characteristic of the flowing atmospheric air, or a combined output signal corresponding to a combined characteristic of the first and second contaminants in the flowing atmospheric air. The characteristic of the first and second contaminant may be of the same type (e.g., concentration), which may be evaluated based on acceptable limit ranges for each of the first and second contaminant or for a combined acceptable limit. In other cases, the characteristics of the first and second contaminant may be different or of the same type but not combinable (e.g., a composition characteristic that is different between the type contaminants). One or more additional ICE devices may be used to detect one or more additional characteristics of the first or second contaminant or may be configured to detect additional contaminants. The ICE devices may generally be configured to detect expected contaminants, such as those described herein.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments herein include:

Embodiment A: A method comprising: optically interacting electromagnetic radiation with a flowing atmospheric air composition; optically interacting the electromagnetic radiation with an integrated computational element ("ICE"), the ICE being configured to analyze for a contaminant in the flowing atmospheric air; receiving with a detector the electromagnetic radiation that has optically interacted with the flowing atmospheric air and the ICE; and generating an output signal corresponding to a characteristic of the contaminant in the flowing atmospheric air.

Embodiment A may have one or more of the following additional elements in any combination:

Element A1: Wherein the ICE is located within an air line extending from an air compressor.

Element A2: Wherein the electromagnetic radiation is at least one selected from the group consisting of infrared radiation, near-infrared radiation, visible light, ultraviolet light, X-ray radiation, and gamma ray radiation.

Element A3: Wherein the electromagnetic radiation is provided by at least one of a light bulb, a light emitting device, a laser, a blackbody, a photonic crystal, an X-Ray source, and a gamma ray source.

Element A4: Wherein the contaminant is selected from the group consisting of an aqueous liquid, an organic liquid, a carbonic acid, a gas, a dry contaminant, a biological contaminant, and any combination thereof.

Element A5: Wherein the characteristic of the contaminant is a concentration of the contaminant in the flowing atmospheric air.

By way of non-limiting example, exemplary combinations applicable to A include: A with A1 and A2; A with A1 and A3; A with A1 and A4; A with A1 and A5; A with A2 and A3; A with A3 and A4; A with A2 and A5; A with A3 and A4; A with A3 and A5; A with A4 and A5; A with A1, A2, and A3; A with A1, A2, A3, A4, and A5; A with A3, A4, and A5.

Embodiment B: A method comprising: optically interacting electromagnetic radiation with a flowing atmospheric air composition; optically interacting the electromagnetic radiation with an integrated computational element ("ICE"), the ICE being configured to analyze for a contaminant in the flowing atmospheric air; receiving with a detector the electromagnetic radiation that has optically interacted with the flowing atmospheric air and the ICE; generating an output signal corresponding to a concentration of the contaminant in the flowing atmospheric air; and determining if the concentration of the contaminant is within an acceptable limit range in the flowing atmospheric air.

Embodiment B may have one or more of the following additional elements in any combination:

Element B1: Wherein the ICE is located within an air line extending from an air compressor.

Element B2: Wherein the electromagnetic radiation is at least one selected from the group consisting of infrared radiation, near-infrared radiation, visible light, ultraviolet light, X-ray radiation, and gamma ray radiation.

Element B3: Wherein the electromagnetic radiation is provided by at least one of a light bulb, a light emitting device, a laser, a blackbody, a photonic crystal, an X-Ray source, and a gamma ray source.

Element B4: Wherein the contaminant is selected from the group consisting of an aqueous liquid, an organic liquid, a carbonic acid, a gas, a dry contaminant, a biological contaminant, and any combination thereof.

Element B5: Wherein the characteristic of the contaminant is a concentration of the contaminant in the flowing atmospheric air.

By way of non-limiting example, exemplary combinations applicable to B include: B with B1 and B2; B with B1 and B3; B with B1 and B4; B with B1 and B5; B with B2 and B3; B with B3 and B4; B with B2 and B5; B with B3 and B4; B with B3 and B5; B with B4 and B5; B with B1, B3, and B5; B with B1, B2, B3, B4, and B5; B with B2, B4, and B5.

Embodiment C: A method comprising: optically interacting electromagnetic radiation with a flowing atmospheric air and optically interacting the electromagnetic radiation with a first integrated computational element ("ICE"), the first ICE configured to analyze for a first contaminant in the flowing atmospheric air; optically interacting the electromagnetic radiation with the flowing atmospheric air and at least a second ICE, the second ICE configured to analyze for a second contaminant in the flowing atmospheric air; receiving with a detector the electromagnetic radiation that has optically interacted with the flowing atmospheric air, the first ICE, and the second ICE; and generating a first output signal corresponding to a characteristic of the first contaminant in the flowing atmospheric air and a second output signal corresponding to a characteristic of the second contaminant in the flowing atmospheric air, or a combined output signal corresponding to a combined characteristic of the first and second contaminants in the flowing atmospheric air.

Embodiment C may have one or more of the following additional elements in any combination:

Element C1: Wherein the ICE is located within an air line extending from an air compressor.

Element C2: Wherein the electromagnetic radiation is at least one selected from the group consisting of infrared radiation, near-infrared radiation, visible light, ultraviolet light, X-ray radiation, and gamma ray radiation.

Element C3: Wherein the electromagnetic radiation is provided by at least one of a light bulb, a light emitting device, a laser, a blackbody, a photonic crystal, an X-Ray source, and a gamma ray source.

Element C4: Wherein the contaminant is selected from the group consisting of an aqueous liquid, an organic liquid, a carbonic acid, a gas, a dry contaminant, a biological contaminant, and any combination thereof.

Element C5: Wherein the characteristic of the first contaminant is a concentration of the first contaminant in the flowing atmospheric air and wherein the characteristic of the second contaminant is a concentration of the second contaminant in the flowing atmospheric air, or where the combined characteristic of the first and second contaminants is a combined concentration of the first and second contaminants in the flowing atmospheric air.

Element C6: Wherein the characteristic of the first contaminant is a concentration of the first contaminant in the flowing atmospheric air and wherein the characteristic of the second contaminant is a concentration of the second contaminant in the flowing atmospheric air, or where the combined characteristic of the first and second contaminants is a combined concentration of the first and second contaminants in the flowing atmospheric air, and further comprising: determining if the concentration of the first contaminant in the flowing atmospheric air is within a first acceptable limit range and/or if the concentration of the second contaminant in the flowing atmospheric air is within a second acceptable limit range, and/or if the concentration of the combined first and second contaminants is within a combined acceptable limit range.

Element C7: Wherein the characteristic of the first contaminant is a concentration of the first contaminant in the flowing atmospheric air and wherein the characteristic of the second contaminant is a concentration of the second contaminant in the flowing atmospheric air, or where the combined characteristic of the first and second contaminants is a combined concentration of the first and second contaminants in the flowing atmospheric air, and further comprising determining if the combined concentration of the first and second contaminants in the flowing atmospheric air is within a combined acceptable limit range.

By way of non-limiting example, exemplary combinations applicable to C include: C with 1 and 2; C with 1 and 3; C with 1 and 4; C with 1 and 5; C with C1 and C6; C with C1 and C7; C with C2 and C3; C with C3 and C4; C with C2 and C5; C with C2 and C6; C with C2 and C7; C with C3 and C4; C with C3 and C5; C with C4 and C5; C with C4 and C6; C with C4 and C7; C with C5 and C6; C with C5 and C7; C with C6 and C7; C with C1, C3, and C5; C with C1, C2, C3, C4, and C5; C with C2, C4, and C7; C with C3, C4, C6, and C7.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. A method comprising:
  optically interacting electromagnetic radiation with a flowing atmospheric air composition;
  optically interacting the electromagnetic radiation with an integrated computational element ("ICE"), the ICE being configured to analyze for a contaminant in the flowing atmospheric air, and
    wherein the ICE is located within an air line extending from an air compressor;
  receiving with a detector the electromagnetic radiation that has optically interacted with the flowing atmospheric air and the ICE; and
  generating an output signal corresponding to a characteristic of the contaminant in the flowing atmospheric air.

2. The method of claim 1, wherein the electromagnetic radiation is at least one selected from the group consisting of infrared radiation, near-infrared radiation, visible light, ultraviolet light, X-ray radiation, and gamma ray radiation.

3. The method of claim 1, wherein the electromagnetic radiation is provided by at least one of a light bulb, a light emitting device, a laser, a blackbody, a photonic crystal, an X-Ray source, and a gamma ray source.

4. The method of claim 1, wherein the contaminant is selected from the group consisting of an aqueous liquid, an organic liquid, a carbonic acid, a gas, a dry contaminant, a biological contaminant, and any combination thereof.

5. The method of claim 1, wherein the characteristic of the contaminant is a concentration of the contaminant in the flowing atmospheric air.

6. A method comprising:
  optically interacting electromagnetic radiation with a flowing atmospheric air composition;
  optically interacting the electromagnetic radiation with an integrated computational element ("ICE"), the ICE being configured to analyze for a contaminant in the flowing atmospheric air, and
    wherein the ICE is located within an air line extending from an air compressor;
  receiving with a detector the electromagnetic radiation that has optically interacted with the flowing atmospheric air and the ICE;
  generating an output signal corresponding to a concentration of the contaminant in the flowing atmospheric air; and
  determining if the concentration of the contaminant is within an acceptable limit range in the flowing atmospheric air.

7. The method of claim 6, wherein the electromagnetic radiation is at least one selected from the group consisting of infrared radiation, near-infrared radiation, visible light, ultraviolet light, X-ray radiation, and gamma ray radiation.

8. The method of claim 6, wherein the electromagnetic radiation is provided by at least one of a light bulb, a light emitting device, a laser, a blackbody, a photonic crystal, an X-Ray source, and a gamma ray source.

9. The method of claim 6, wherein the contaminant is selected from the group consisting of an aqueous liquid, an organic liquid, a carbonic acid, a gas, a dry contaminant, a biological contaminant, and any combination thereof.

10. The method of claim 6, wherein the characteristic of the contaminant is a concentration of the contaminant in the flowing atmospheric air.

11. A method comprising:
  optically interacting electromagnetic radiation with a flowing atmospheric air and optically interacting the electromagnetic radiation with a first integrated computational element ("ICE"), the first ICE configured to analyze for a first contaminant in the flowing atmospheric air;
  optically interacting the electromagnetic radiation with the flowing atmospheric air and at least a second ICE, the second ICE configured to analyze for a second contaminant in the flowing atmospheric air, and
    wherein the first ICE and the second ICE are located within an air line extending from an air compressor and connected to at least one selected from the group consisting of a tank comprising a powder composition, a tank comprising a treatment fluid, a clean room, purification equipment, and any combination thereof;
  receiving with a detector the electromagnetic radiation that has optically interacted with the flowing atmospheric air, the first ICE, and the second ICE; and
  generating a first output signal corresponding to a characteristic of the first contaminant in the flowing atmospheric air and a second output signal corresponding to a characteristic of the second contaminant in the flowing atmospheric air, or a combined output signal corresponding to a combined characteristic of the first and second contaminants in the flowing atmospheric air.

12. The method of claim 11, wherein the electromagnetic radiation is at least one selected from the group consisting of infrared radiation, near-infrared radiation, visible light, ultraviolet light, X-ray radiation, and gamma ray radiation.

13. The method of claim 11, wherein the electromagnetic radiation is provided by at least one of a light bulb, a light emitting device, a laser, a blackbody, a photonic crystal, an X-Ray source, and a gamma ray source.

14. The method of claim 11, wherein the contaminant is selected from the group consisting of an aqueous liquid, an organic liquid, a carbonic acid, a gas, a dry contaminant, a biological contaminant, and any combination thereof.

15. The method of claim 11, wherein the characteristic of the first contaminant is a concentration of the first contaminant in the flowing atmospheric air and wherein the characteristic of the second contaminant is a concentration of the second contaminant in the flowing atmospheric air, or where the combined characteristic of the first and second contaminants is a combined concentration of the first and second contaminants in the flowing atmospheric air.

16. The method of claim 15, further comprising:
  determining if the concentration of the first contaminant in the flowing atmospheric air is within a first acceptable limit range and/or if the concentration of the second contaminant in the flowing atmospheric air is within a second acceptable limit range, and/or if the concentration of the combined first and second contaminants is within a combined acceptable limit range.

17. The method of claim 15, further comprising:
determining if the combined concentration of the first and second contaminants in the flowing atmospheric air is within a combined acceptable limit range.

* * * * *